United States Patent
Tracy et al.

(10) Patent No.: US 11,918,019 B2
(45) Date of Patent: Mar. 5, 2024

(54) FOOD COMPONENTS HAVING HIGH PROTEIN CONTENT

(71) Applicant: SUPERBREWED FOOD, INC., New Castle, DE (US)

(72) Inventors: Bryan P. Tracy, Wilmington, DE (US); Aharon M. Eyal, Jerusalem (IL); Sasson Somekh, Los Altos Hills, CA (US); Shawn Jones, Bear, DE (US); Daniel Knox Mitchell, Wilmington, DE (US); Alon Karpol, Tel Mond (IL); Kartheek Ankella-Anderson, Cranston, RI (US)

(73) Assignee: SUPERBREWED FOOD INC., New Castle, DE (US)

( * ) Notice: Subject to any disclaimer, the term of this patent is extended or adjusted under 35 U.S.C. 154(b) by 0 days.

(21) Appl. No.: 18/022,282

(22) PCT Filed: Aug. 22, 2021

(86) PCT No.: PCT/IB2021/057696
§ 371 (c)(1),
(2) Date: Feb. 21, 2023

(87) PCT Pub. No.: WO2022/043847
PCT Pub. Date: Mar. 3, 2022

(65) Prior Publication Data
US 2023/0320399 A1    Oct. 12, 2023

Related U.S. Application Data

(60) Provisional application No. 63/208,017, filed on Jun. 8, 2021, provisional application No. 63/183,273, filed on May 3, 2021, provisional application No. 63/069,087, filed on Aug. 23, 2020.

(51) Int. Cl.
*C12N 1/20* (2006.01)
*A23C 11/10* (2021.01)
*A23C 20/02* (2021.01)
*A23J 1/00* (2006.01)
*A23J 3/20* (2006.01)
*A23J 3/22* (2006.01)
*A23L 33/135* (2016.01)
*A23L 33/195* (2016.01)

(52) U.S. Cl.
CPC ............ *A23L 33/195* (2016.08); *A23C 11/10* (2013.01); *A23C 11/103* (2013.01); *A23C 20/02* (2013.01); *A23J 1/008* (2013.01); *A23J 3/20* (2013.01); *A23J 3/227* (2013.01); *A23L 33/135* (2016.08); *C12N 1/20* (2013.01)

(58) Field of Classification Search
CPC ...... A23L 33/195; A23L 33/135; A23C 11/10; A23C 11/103; A23C 20/02; A23J 1/008; A23J 3/20; A23J 3/27; A23J 3/227; C12N 1/20
USPC .............................................. 426/7
See application file for complete search history.

(56) References Cited

U.S. PATENT DOCUMENTS

2015/0305361 A1* 10/2015 Holz-Schietinger .... A23L 25/40
                                                                        426/62
2019/0352676 A1* 11/2019 Senaratne ................ C12N 1/06

* cited by examiner

*Primary Examiner* — Hamid R Badr
(74) *Attorney, Agent, or Firm* — Eva Leah Taksel

(57) ABSTRACT

Provided is food component comprising cells of at least one bacterium, said cells comprising a crude protein concentration of at least 60 wt % of a total dry weight of said cells and nucleic acid at a concentration of less than about 5 wt % of a total dry weight of said cells, wherein at least 50% of a total number of said cells are dead cells. Further provided are food and beverages comprising such food components and methods of manufacture thereof.

20 Claims, No Drawings

FOOD COMPONENTS HAVING HIGH PROTEIN CONTENT

CROSS-REFERENCE TO RELATED APPLICATION

The present application gains priority from U.S. Provisional Applications No. 63/069,087 filed Aug. 23, 2020; No. 63/183,273 filed May 3, 2021; and No. 63/208,017 filed Jun. 8, 2021 which are incorporated by reference as if fully set-forth herein.

FIELD OF THE INVENTION

The present invention, in at least some embodiments, relates to food components having high protein content and more specifically to a food component comprising bacterial cells having a crude protein concentration of at least 60 wt %, wherein at least 50% of said cells are dead cells, said cells having a nucleic acid concentration of less than about 5 wt %.

BACKGROUND OF THE INVENTION

Proteins are molecules essential to the structure and function of all living organisms. Protein sources include meat, casein and whey (milk proteins), gelatin, soybean, yeast, and grains.

Analogues of dairy and meat products, generally based on vegetable proteins, are known in the art and are becoming increasingly in demand by consumers such as those suffering from lactose intolerance or due to ethical considerations regarding exploitation of animals by the dairy and meat industries and environmental impact of animal farming.

Dairy analogues, such as non-dairy cheese analogues, generally based on vegetable proteins, are known in the art and are becoming increasingly in demand by consumers such as those suffering from lactose intolerance or due to ethical considerations regarding exploitation of animals by the dairy industry and environmental impact of dairy farming.

Known milk analogues, such as almond milk, have low protein contents as compared to animal milk, while known cheese and meat analogues commonly have undesirable flavors and/or textures.

SUMMARY OF THE INVENTION

According to an aspect of some embodiments of the present invention, there is provided food component comprising cells of at least one bacterium, said cells comprising a crude protein concentration of at least 60 wt % of a total dry weight of said cells and a nucleic acid concentration of less than about 5 wt % of a total dry weight of said cells, wherein at least 50% of a total number of said cells are dead cells.

DETAILED DESCRIPTION OF THE INVENTION

The present invention, in at least some embodiments thereof, relates to food components having high protein content and more specifically to a food component comprising bacterial cells having a crude protein content of at least 60 wt % of a total dry weight of the cells, wherein at least 50% of said cells are dead cells, said cells having a nucleic acid concentration of less than about 5 wt % of a total dry weight of the cells. The use of dead cells enables bacterial proteins to be provided to a subject without affecting the microbiome of the subject, in contrast to the use of live probiotic cells which may affect the microbial balance of the gastrointestinal system of the subject.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

As used herein, the term "food component" refers to an ingestible constituent of a food or beverage, such as an additive for a food or beverage; an ingredient of a food or beverage; or a concentrated composition from which a food or beverage is prepared.

As used herein, the term "dairy analogue" refers to a non-dairy or vegan product having a similar flavor and texture to that of a conventional dairy product. In some embodiments, the dairy analogue is an analogue of a cheese i.e. an analogue of a cheese formed by coagulation of the milk protein casein.

As used herein, the term "modified starch" refers to a starch extracted from grains or vegetables which has been physically, enzymatically or chemically treated to change at least one property as compared to the native starch.

As used herein, the term "native starch" refers to a starch extracted from grains or vegetables which has not been treated physically, enzymatically, or chemically.

As used herein, the term "fat" refers to a triglyceride having a melting point which is equal to or greater than room temperature, such that the triglyceride is solid or semi-solid at room temperature, wherein room temperature is considered to be in the range of 20-25° C.

As used herein, the term "foam" refers to a two-phase system in which gas cells are enclosed by liquid.

As used herein, the term "single-cell protein" refers to a crude or refined protein originating from a unicellular organism.

As used herein, the term "within a cell structure" with regard to a protein refers to protein present in any intercellular location, in contrast to extracellular protein which may be excreted from a cell or released from the cell following cell lysis.

As used herein, the term "intact cell" refers to a non-lysed cell.

As used herein, the term "vegetable protein" refers to a protein present in or isolated from a vegetable.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

As used herein, when a numerical value is preceded by the term "about", the term "about" is intended to indicate +/−10% of that value.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

According to an aspect of some embodiments of the present invention, there is provided a food component comprising cells of at least one bacterium, said cells comprising a crude protein concentration of at least 60 wt % of a total dry weight of said cells and nucleic acid at a concentration of less than about 5 wt % of a total dry weight of said cells, wherein at least 50% of a total number of said cells are dead cells.

According to some embodiments, said crude protein concentration is at least 60 wt %, at least 65 wt %, at least 70 wt %, at least 75 wt %, at least 80 wt %, at least 85 wt %, at least 90 wt % or at least 95 wt % of said total dry weight of said cells. According to a preferred embodiment, said crude protein concentration is at least 80 wt % of said total dry weight of said cells.

According to some embodiments, at least 50%, at least 55%, at least 60%, at least 65%, at least 70%, at least 75%, at least 80%, at least 85%, at least 90%, at least 95% or even 100% of a total number of cells in said food component are dead cells.

According to some embodiments, said nucleic acid concentration is less than 5 wt %, less than 4 wt %, less than 3 wt %, less than 2 wt %, less than 1 wt %, less than 0.5 wt % or even less than 0.1 wt % of a total dry weight of said cells.

According to some embodiments, nucleic acid is removed by heat treatment of the cells, such as, for example, by exposure to a temperature of about 70° C. for about 20. In some such embodiments, the cells are washed at least once, such as once, twice or three times, following heat treatment.

According to some embodiments, most of the proteins (such as enzymes, structural proteins, transporters, channels, etc.) present in the cells (including proteases) but with the exception of DNAase and RNAase, are denatured following heat treatment. According to some embodiments, the cells are substantially devoid of activity of enzymes other than DNAase and/or RNAase.

According to some embodiments, said cells have a protease activity of about 1 milli Anson Unit, wherein 1 mili Anson Unit is defined as the amount of enzyme that liberates 1 μmol of trichloracetic acid (TCA)-soluble, Folin-positive amino acids within 1 minute at pH 7.5 and 37° C., using hemoglobin as a substrate.

According to some embodiments, said at least one bacterium is an anaerobic bacterium.

According to some embodiments, said at least one bacterium is a Gram-positive bacterium. According to some such embodiments, said Gram-positive bacterium is of the class Clostridia, such as Clostridium tyrobutyricum.

According to some embodiments, at least 50 wt % of said cells are intact cells.

According to some embodiments, at least 50% of said cells are lysed cells.

According to some embodiments, said cells further comprise essential amino acids at a concentration of from about 10 wt % to about 50 wt % of a total dry weight of said cells. According to some such embodiments, the concentration of essential amino acids is at least 10 wt %, at least 15 wt %, at least 20 wt %, at least 25 wt %, at least 30 wt %, at least 35 wt %, at least 40 wt %, at least 45 wt % or up to about 50 wt % of a total dry weight of said cells.

According to some embodiments, said cells further comprise branched chain amino acids at a concentration of from about 10 wt % to about 25 wt % of a total dry weight of said cells. According to some such embodiments, the concentration of branched chain amino acids is about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt % or about 25 wt % of a total dry weight of said cells.

According to some embodiments, said cells comprise at least one amino acid is selected from the group consisting of lysine, methionine, threonine, histidine, leucine, isoleucine, aspartic acid/asparagine, glutamic acid/glutamine, serine, glycine, arginine, alanine, tyrosine, valine, phenylalanine, proline, cysteine, tryptophan and combinations thereof. According to some embodiments, said amino acid is an essential amino acid According to some embodiments, the food component has a moisture content of no greater than 20 wt %. According to some such embodiments, the moisture content is less than 20 wt %, less than 15 wt %, less than 10 wt % or even less than 5 wt % of the total food component.

According to some embodiments, the food component further comprises at least one mineral selected from the group consisting of calcium, iron, zinc, copper, manganese, molybdenum, selenium and combinations thereof.

According to some embodiments, said cells further comprises Vitamin B12 at a concentration of from about 1 to about 20 microgram (mcg) per 100 gram dry weight of cells, such as about 1 mcg, about 2 mcg, about 3 mcg, about 4 mcg, about mcg, about 6 mcg, about 7 mcg, about 8 mcg, about 9 mcg, about 10 mcg, about 11 mcg, about 12 mcg, about 13 mcg, about 14 mcg, about 15 mcg, about 16 mcg, about 17 mcg, about 18 mcg, about 19 mcg or about 20 mcg per 100 gram dry weight of said cells.

According to some embodiments, said cells comprise from peptidoglycan at a concentration of from about 0.1 to about 10 wt % of a total dry weight of said cells.

According to some embodiments, said food component is in the form of a powder. According to some such embodiments, said powder comprises particles of size of from about 10 to about 500 microns, such as about 10 microns, about 20 microns, about 30 microns, about 40 microns, about 50 microns, about 100 microns, about 150 microns, about 200 microns, about 250 microns, about 300 microns, about 350 microns, about 400 microns, about 450 microns or about 500 microns.

According to some embodiments, said food component is provided as a partially-dried product, having a water content of from about 20 wt % to about 80 wt % of the total weight of the food component, such as about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, or about 80 wt % of the total weight of the food component.

According to some embodiments, said cells comprise fat at a concentration of less than about 1 wt % of a total dry weight of said cells, such as less than about 1 wt %, less than about 0.5 wt %, less than about 0.1 wt % of the total dry weight of said cells.

According to some embodiments, said cells have a butyric acid concentration of from about 0.001 wt % to about 1 wt % of the total weight of said cells, such as about 0.01 wt %, about 0.005 wt %, about 0.01 wt %, about 0.05 wt %, about 0.1 wt %, about 0.5 wt % or about 1 wt % of the total weight of said cells. According to some such embodiments, the food component has a pH of greater than about 6.7, such as 6.8, 6.9, 7.0, 7.1, 7.2, 7.3 or 7.4. According to some such embodiments, the food or beverage has a pH of less than about 7.5.

According to some embodiments, said bacterium is a naturally occurring bacterium.

According to some embodiments, said food component comprises less than about 0.1 wt % casein. According to some embodiments, said food component is substantially devoid of casein.

According to some embodiments, said food component is substantially devoid of an undesirable flavor. The presence of an undesirable flavor may be determined, for example, by one or more professional tasters skilled in the art of flavor determination.

According to some embodiments, the food component is white in color.

According to an aspect of some embodiments, there is provided a food additive comprising the food component as disclosed herein. According to some such embodiments, the food additive is configured for addition to a food or beverage, such as for example to a dairy food product, a non-dairy food product (including a dairy analogue), a vegetable food product, a meat product. The additive may, for example, be used to increase the total protein content of the food or beverage.

According to some such embodiments, the food additive is provided in powder form. According to some embodiments, the food additive is provided as a partially-dried product, having a water content of less than about 10 wt % of the total weight of the food additive, such as less than about 10 wt %, less than about 9 wt %, less than about 8 wt %, less than about 7 wt %, less than about 6 wt %, less than about 5 wt %, less than about 4 wt %, less than about 3 wt %, less than about 2 wt % or less than about 1 wt % of the total weight of the food additive.

According to some embodiments, the food additive is added to a food or beverage in an amount of from about 1 wt % to about 20 wt % of the final weight of the food or beverage, such as about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 18 wt % or about 20 wt % of the final weight of the food or beverage.

According to an aspect of some embodiments, there is provided a food ingredient comprising the food component as disclosed herein. According to some embodiments, the food ingredient is provided in a ready-to-mix form to which one or more ingredients are to be added to obtain a final food or beverage product. According to some such embodiments, the food ingredient is configured for combination with other ingredients for preparation of a food or beverage, such as for example a non-dairy food or beverage (including a dairy analogue). According to some such embodiments, the food ingredient is provided in powder form. According to some embodiments, the food ingredient is provided as a partially-dried product, having a water content of less than about 10 wt % of the total weight of the food ingredient, such as less than about 10 wt %, less than about 9 wt %, less than about 8 wt %, less than about 7 wt %, less than about 6 wt %, less than about 5 wt %, less than about 4 wt %, less than about 3 wt %, less than about 2 wt % or less than about 1 wt % of the total weight of the food ingredient. According to some embodiments, the food ingredient is configured for combination with a liquid base, such as milk, a milk analogue or water, for preparation of a beverage. According to some embodiments, the food ingredient is configured for combination with a milk analogue such as oat milk, a nut milk (such as almond milk), soy milk, rice milk and combinations thereof.

According to some embodiments, the food ingredient is added to a food or beverage in an amount of from about 1 wt % to about 50 wt % of the final weight of the food or beverage, such as about 1 wt %, about 5 wt %, about 10 wt %, about 15 wt %, about 20 wt %, about 25 wt %, about 30 wt %, about 35 wt %, about 40 wt %, about 45 wt %, or about 50 wt % of the final weight of the food or beverage.

According to an aspect of some embodiments of the present invention, there is provided a food binder comprising the food component or the food additive as disclosed herein. According to some such embodiments, the food binder is for use as a binder in a meat, fish or dairy analogue.

According to some embodiments, there is provided a meat analogue comprising the food binder as disclosed herein. According to some such embodiments, the food binder is present in the meat analogue at a concentration of from about 1 wt % to about 10 wt %, such as about 1 wt %, about 2 wt %, about 3 wt %, about 4 wt %, about 5 wt %, about 6 wt %, about 7 wt %, about 8 wt %, about 9 wt % or about 10 wt % of the total weight of the meat analogue.

The use of the food component of the present invention as a binder for meat analogue, particularly extruded meat analogues, is considered to be a preferred alternative to the use of known binders, such as methyl cellulose for such applications. According to some embodiments, the meat analogue has a methyl cellulose content of less than about 1 wt % of the total weight of the meat analogue, such as about 1 wt %, about 0.9 wt %, about 0.8 wt %, about 0.7 wt %, about 0.6 wt %, about 0.5 wt %, about 0.4 wt %, about 0.3 wt %, about 0.2 wt %, about 0.1 wt % or less than 0.1 wt %.

According to an aspect of some embodiments, there is provided a food or beverage comprising the food component as disclosed herein. According to some embodiments, the food component is added to a liquid base, such as water, milk or a non-dairy milk analogue to obtain a ready-to-drink beverage or protein supplement.

According to some embodiments, said food component provides at least 60 wt % of the total protein present in the food or beverage. According to some such embodiments, the food component provides at least 60 wt %, at least 65 wt %, at least 70 wt %, at least 75 wt %, at least 80 wt %, at least 85 wt % or at least 90 wt % of the total protein present in the food or beverage.

According to some embodiments, the food or beverage is a dairy analogue. According to some such embodiments, the dairy analogue is a vegan product.

According to an aspect of some embodiments of the present invention, there is provided a dairy analogue having a high total protein content, wherein at least 60 wt % of the total protein content of the dairy analogue comprises single-cell protein.

According to some embodiments, said single-cell protein is solvent extracted single-cell protein. According to some embodiments, said solvent-extracted single-cell protein is devoid of an undesirable taste. According to some embodiments, the solvent used for said extraction is selected from the group consisting of hexane, ethanol and combinations thereof.

According to some embodiments, said single-cell protein is milled single-cell protein. According to some such embodiments, said single-cell protein is milled to an average particle diameter of less than 20 microns, less than 15 microns, less than 10 microns or even less than 5 microns.

According to some embodiments, at least 60 wt % of the total protein content of the dairy analogue comprises single-cell protein.

According to some embodiments, said total protein content is between 3 wt % and 20 wt % of the total weight of the dairy analogue, such as 3 wt %, 4 wt %, 5 wt %, 10 wt %, 15 wt % or 20 wt %.

According to some embodiments, at least 60 wt %, at least 65 wt %, at least 70 wt %, at least 75 wt %, at least 80 wt %, at least 85 wt %, at least 90 wt %, at least 95 wt % or even 100 wt % of the total protein content of the dairy analogue comprises single-cell protein.

According to some embodiments, the dairy analogue is devoid of casein.

According to some embodiments, said total protein content is between 3% and 20 wt % of the dairy analogue, such as 3%, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt % or 20 wt % of the dairy analogue.

According to some embodiments, at least 50 wt %, such as 50 wt %, at least 55 wt %, at least 60 wt %, at least 65 wt %, at least 70 wt %, at least 75 wt %, at least 80 wt %, at least 85 wt %, at least 90 wt %, at least 95 wt % or even 100 wt % of said single-cell protein is provided within a cell structure of a unicellular organism producing said single-cell protein.

According so some such embodiments, wherein the dairy analogue is a non-dairy analogue of a cheese product, the dairy analogue further comprises modified starch and fat.

Currently known non-dairy cheese analogues are generally considered to be greatly inferior to milk-derived cheeses in flavor and texture as well as in their ability to be grated, melted etc. for cooking purposes. This is primarily due to the fact that vegetable proteins generate rigid crosslinks that result in a texture resembling that of tofu.

It is known to modify starch to provide a product having suitable physical properties for melting. However, when combined with vegetable protein, the resultant product has been found to be unable to retain its form and is therefore too soft prior to melting.

The present inventors have surprisingly found that when single-cell proteins are used as the major protein source in a non-dairy cheese analogue, together with modified starch, the desirable properties of the modified starch are retained.

Without wishing to be bound by any one theory, the present inventors have hypothesized that the single-cell protein does not contribute to the desirable properties of the modified starch, but rather does not interfere with the properties of the starch, in contrast to vegetable proteins.

According to some embodiments, said protein is provided within an intact cell of a unicellular organism producing said single-cell protein.

According to some embodiments, said organism is a Clostridia class bacterium.

According to some embodiments, said organism comprises at least 70 wt % protein, such as 70 wt %, at least 75 wt %, at least 80 wt %, at least 85 wt %, at least 90 wt %, at least 95 wt % or even 100 wt % crude protein.

According to some embodiments, said modified starch is selected from the group consisting of potato starch, corn starch, rice starch, wheat starch and combinations thereof. According to some such embodiments, said modified starch comprises potato starch.

According to some embodiments, said modified starch is present in the dairy analogue at a concentration of about 15 wt % of the total product.

According to some embodiments, said fat is selected from the group consisting of coconut oil, palm oil, canola oil, sunflower oil, cocoa butter and combinations thereof. According to some embodiments, the dairy analogue further comprises a vegetable protein. According to some embodiments, said vegetable protein comprises a protein obtained from a vegetable selected from the group consisting of a legume, including beans (such as soy beans), lentils, chickpeas and peas. According to some embodiments, said vegetable protein comprises wheat protein.

According to some embodiments, one tablespoon (15 g) of said food component provides at least about 10 g (such as about 10 g, about 11 g, about 12 g, about 13 g, about 14 g or even about 15 g) of complete protein; about 100% recommended daily intake value (DV) of Vitamin B12; at least 10% DV of iron (such as at least 10%, at least 11%, at least 12%, at least 13%, at least 14%, or at least 15%) for a female or at least 30% of DV (such as at least 30%, at least 31%, at least 32%, at least 33%, at least 34%, or at least 35%) for a male; at least 5% DV (such as about 5%, about 6%, about 7%, about 8%, about 9% or about 10%) of Vitamin B2; and about 100% DV of butyrate. In a preferred embodiment, one tablespoon (15 g) of said food component provides about 12 g complete protein, about 100% DV of Vitamin B12, about 15% DV of iron for a female or about 35% DV of iron for a male, about 10% DV of Vitamin B2 and about 100 DV of butyrate.

According to some embodiments, said dairy analogue is a vegan analogue of a dairy product selected from the group consisting of a cheese (including a hard cheese, a soft cheese, a semi-soft cheese and a spreadable cheese), a milk beverage, a yoghurt, a cream (including a sour cream or a sweet cream), a whipped cream, an ice-cream, a dessert and a butter.

According to some embodiments, said analogue of a cheese is provided in block form or shredded form. According to some embodiments, said analogue of a cheese is provided in the form of slices, wedges, cubes, triangles and other suitable forms.

Non-limiting examples of hard cheeses include Cheddar, Gouda, Parmesan, Gruyere, Emmental, Provolone, Caciocavallo, Queso Oaxaca, Scamorza, Ragusano, Kashkavel and the like. Non-limiting examples of soft cheeses include Brie, Camembert, cream cheese, cottage cheese and the like. Non-limiting examples of semi-soft cheeses include Mozzarella. According to some embodiments, said analogue of a milk beverage is an analogue of a beverage selected from the group consisting of milk, a milk shake and a protein shake.

According to some embodiments, said analogue of a milk beverage comprises a milk analogue selected from the group consisting of a milk analogue such as oat milk, a nut milk (such as almond milk), soy milk, rice milk, coconut milk and combinations thereof.

According to some embodiments, said analogue of a milk beverage has a protein concentration of from about 2 wt % to about 20 wt % of the total weight of the beverage, such as about 2 wt %, about 4 wt %, about 6 wt %, about 8 wt %, about 10 wt %, about 12 wt %, about 14 wt %, about 16 wt %, about 18 wt % or about 20 wt % of the total weight of the beverage.

According to some embodiments, said analogue of a milk beverage further comprises a natural or artificial flavorant, including, for example, a fruit extract, vanilla, honey, sugar or combinations thereof.

According to some embodiments, said analogue of a milk beverage further comprises at least one selected from the group consisting of coffee, cocoa, chocolate and combinations thereof.

According to some embodiments, said analogue of a milk beverage further comprises a fruit. According to some such embodiments, said fruit is present in the form of a fruit extract, a fruit juice concentrate, as solid pieces of fruit or the like.

According to some embodiments, the food or beverage further comprises from about 0.5 wt % to about 30 wt % fat of the total weight of the food or beverage, such as about 0.5 wt %, about 1 wt %, about 5 wt %, about 10 wt %, about 15 wt %, about 20 wt %, about 25 wt % or about 30 wt % of the total weight of the food or beverage. According to some embodiments, said fat is selected from the group consisting of coconut oil, palm oil, canola oil, sunflower oil and combinations thereof.

According to some embodiments, the food or beverage further comprises from about 5 to about 20 wt % carbohydrate of the total weight of the food or beverage, such as about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt % or about 20 wt % of the total weight of the food or beverage. According to some such embodiments, said carbohydrate comprises modified starch. According to some such embodiments, said carbohydrate comprises native starch. According to some embodiments, said starch (modified or native) is selected from the group consisting of potato starch, corn starch, rice starch, wheat starch and combinations thereof. According to a preferred embodiment, said starch is potato starch.

According to some embodiments, the food or beverage further comprises at least one amino acid. According to some such embodiments, said at least one amino acid is selected from the group consisting of lysine, methionine, threonine, histidine, leucine, isoleucine, aspartic acid/asparagine, glutamic acid/glutamine, serine, glycine, arginine, alanine, tyrosine, valine, phenylalanine, proline, cysteine, tryptophan and combinations thereof. According to some embodiments, said amino acid is an essential amino acid.

According to some embodiments, said food or beverage comprises an oil-in-water emulsion, wherein said protein stabilizes said emulsion on the interface of oil droplets.

According to some embodiments, said food or beverage is a homogenized product.

According to some embodiments, said food or beverage further comprises an edible oil. According to some embodiments, said edible oil is selected from the group consisting of palm oil, canola oil, corn oil, linseed oil, soybean oil, safflower oil, sunflower oil, avocado oil, mustard oil, peanut oil, sesame oil and combinations thereof. According to some embodiments, wherein the food is a hard cheese, the edible oil is solid at ambient temperature. According to some embodiments, wherein the food is a soft or semi-soft cheese, the edible oil is semi-soft at ambient temperature.

According to some embodiments, the food or beverage comprises a foam.

According to some embodiments, the food or beverage comprises dispersed particles of said bacterium.

According to some embodiments, the food or beverage further comprises at least 0.05 wt % of butyrate and/or butyrin. According to some such embodiments, the food or beverage has a pH of greater than about 6.7, such as 6.8, 6.9, 7.0, 7.1, 7.2, 7.3 or 7.4. According to some such embodiments, the food or beverage has a pH of less than about 7.5.

According to some embodiments, the food component as disclosed herein provides at least 50 wt % of the total protein content of the food or beverage, such as about 50 wt %, about 55 wt %, about 60 wt %, about 65 wt %, about 70 wt %, about 75 wt %, about 80 wt %, about 85 wt %, about 90 wt %, about 95 wt % or even about 100 wt % of the total protein in the food or beverage.

According to some embodiments, the food or beverage further comprises a plant protein, such as a vegetable protein obtained by fermenting at least a part of a vegetable plant, at a concentration of from about 20 wt % to about 80 wt % of the total protein content, such as about 20 wt %, about 25 wt %, about 30 wt %, about 35 wt %, about 40 wt %, about 45 wt %, about 50 wt %, about 55 wt %, about 60 wt %, about 70 wt %, about 75 wt % or about 80 wt % of the weight of the total protein content of the food or beverage. According to some such embodiments, said plant protein is obtained from a plant selected from the group consisting of oats; wheat; nuts (such as almonds); legumes including beans (such as soy beans), lentils, chickpeas and peas; rice and combinations thereof.

According to some embodiments, the food is a meat or fish analogue, such as an analogue of beef, chicken, turkey, or pork. According to some embodiments, the meat or fish analogue is an extruded meat or fish analogue. According to some embodiments, the meat or fish analogue may be provided in the form of a steak. According to some embodiments, the meat or fish analogue may be provided in a ready-to-cook or a ready-to-heat (i.e. pre-cooked) form, such as an analogue of meatballs or fish-balls, fish-sticks, sausages, steak, hamburgers or the like. According to some embodiments, the meat or fish analogue may be provided in the form of a schnitzel or a nugget, further comprising a coating of breadcrumbs, non-gluten crumb coating or the like.

According to some embodiments, the meat or fish analogue has a protein concentration of from about 5 wt % to about 40 wt % of the total weight of the food, such as about 5 wt %, about 10 wt %, about 15 wt %, about 20 wt %, about 25 wt %, about 30 wt %, about 35 wt % or about 40 wt % of the total weight of the food.

According to some embodiments, the meat or fish analogue comprises fat at a concentration of from about 5 wt % to about 20 wt % of the total weight of the food, such as from about 5 wt %, about 10 wt %, about 15 wt % or about 20 wt % of the total weight of the food. According to some embodiments, at least 50 wt % of the total fat comprises saturated fat, such as about 50 wt %, about 55 wt %, about 60 wt %, about 65 wt %, about 70 wt %, about 75 wt %, about 80 wt %, about 85 wt % about 90 wt %, about 95 wt % or even about 100 wt % of the total fat. According to some such embodiments, said fat is selected from the group consisting of coconut oil, palm oil, canola oil, sunflower oil, cocoa butter and combinations thereof.

According to some embodiments, the meat or fish analogue comprises carbohydrate at a concentration of from about 0.5 wt % to about 5 wt % carbohydrate of the total weight of the food, such as about 0.5 wt %, about 1 wt %, about 2 wt %, about 3 wt %, about 3.5 wt %, about 4 wt %, about 4.5 wt % or about 5 wt %.

According to some embodiments, said meat or fish analogue comprises at least one amino acid. According to some embodiments, said at least one amino acid is selected from the group consisting of lysine, methionine, threonine, histidine, leucine, isoleucine, aspartic acid/asparagine, glutamic acid/glutamine, serine, glycine, arginine, alanine, tyrosine, valine, phenylalanine, proline, cysteine, tryptophan and combinations thereof. According to some embodiments, said amino acid is an essential amino acid.

According to some embodiments, said meat or fish analogue further comprises an edible oil.

According to some embodiments, said meat or fish analogue further comprises at least 0.05 wt % of butyrate and/or butyrin of the total weight of the food. According to some such embodiments, the meat or fish analogue has a pH of greater than about 6.7, such as 6.8, 6.9, 7.0, 7.1, 7.2, 7.3 or 7.4. According to some such embodiments, the food or beverage has a pH of less than about 7.5.

According to some embodiments, the meat or fish analogue further comprises a plant protein at a concentration of from about 20 wt % to about 80 wt % of the total protein content, such as about 20 wt %, about 25 wt %, about 30 wt %, about 35 wt %, about 40 wt %, about 45 wt %, about 50 wt %, about 55 wt %, about 60 wt %, about 70 wt %, about 75 wt % or about 80 wt % of the weight of the total protein content of the food or beverage. According to some such embodiments, said plant protein is selected from the group consisting of an oat protein, a nut protein, a soy protein and combinations thereof.

According to some embodiments, the food is a baked item, such as a cake, cupcake, muffin, biscuit, bread, bread roll, pitta bread comprising the food component of the present invention.

According to some embodiments, the food is an item of confectionery such as a sweet, a toffee, a chocolate comprising the food component of the present invention.

According to some embodiments, the food is an energy bar comprising the food component of the present invention.

According to some embodiments, there is provided an analogue of a milk beverage comprising the food component as disclosed herein and a plant-based milk. According to some embodiments, the plant-based milk is oat milk. According to some embodiments, the plant-based milk is almond milk.

According to an aspect of some embodiments of the present invention, there is provided a method for the manufacture of the food component as disclosed herein, the method comprising culturing cells of bacteria in a fermentation medium to obtain a fermentation medium comprising a biomass; separating said biomass from said fermentation medium containing said biomass to obtain separated biomass; and killing at least 50% of cells of said separated biomass.

According to some embodiments, said separating comprises microfiltration.

According to some embodiments, said killing comprises pasteurizing said separated biomass.

According to some embodiments, the method further comprises lysing said cells. According to some embodiments, lysing comprises at least one of spray drying and French press cell lysis.

According to some embodiments, the method further comprises heating said separated biomass to a temperature of at least 135° C. for a period of at least 2-3 seconds (UHT Past).

According to some embodiments, the method further comprises drying said separated biomass to provide a dry biomass having a water content of no greater than 5 wt %. According to some such embodiments, drying is carried out by a method selected from the group consisting of spray drying, dual drum drying and freeze drying.

According to some embodiments, the method further comprises milling, such as by pulverizing, said dry biomass to a particle size of from about 1 microns to about 150 microns, such as about 1 micron, about 5 microns, about 10 microns, about 15 microns, about 20 microns, about 25 microns, about 50 microns, about 75 microns, about 100 microns, about 125 microns or about 150 microns.

According to some embodiments, the method further comprises washing said separated biomass with water to obtain a solution comprising washed cells and drying said washed cells to obtain a washed biomass.

According to some embodiments, the method further comprises blending said food ingredient with a plant-based milk to form a blend and optionally homogenizing said blend.

EXAMPLES

Example 1: Preparation of the Food Component of the Present Invention by Fermentation A seed fermentation is conducted in which 6 tubes, each containing 10 mL of growth media are inoculated with a single Clostridia cryotube from a master cell bank.

The fermentation is allowed to continue for 16 hours, after which the contents of the 10 mL tubes are used to inoculate 3 bottles, each containing 800 mL of growth media.

The fermentation continues for 8 hours after which the contents of the 3 bottles are used to inoculate a 50 L fermentor.

After fermentation for 8 hours, the contents of the 50 L fermentor are used to inoculate the final seed fermentation, in a 1,000 L vessel.

After fermentation for 8 hours, the contents of the 1,000 L fermentor is used to inoculate the main fermentor, in a 18,000 L vessel. The fermentation continues until all sugar in the fermentor is depleted.

The pH and temperature are monitored continuously to ensure the efficiency of the fermentation. The fermentation is anaerobic and oxygen is excluded from the process. Consumption of sugars is monitored during the fermentation processes.

The temperature is set at 30-36° C. for the duration of the fermentation process with an acceptable range of between 20 and 40° C. The pH of the fermentation process is set to 5.8 and the range 5.4 to 6.5 is considered acceptable. pH is adjusted by addition of hydrochloride acid or ammonium hydroxide.

Cell concentration is measured by monitoring optical density using UV-Vis spectrophotometry. The minimal value is 30 AU. The composition of the broth is also monitored during the fermentation process.

At the end of the fermentation, the cell mass is separated from the fermentation broth and concentrated to 15% total solids by microfiltration. The cell mas is heated to 70° C. for 20 minutes to inactivate proteases activity, and to accelerate DNA and RNA degradation into nucleotides. The cells and the nucleotides are then washed using a counter-current flow of water and microfiltration is performed over 2 stages. The cell mass is then again separated from the wash on the microfiltration and dried on a drum dryer or a spray dryer. To further reduce particle size, the powder is milled or pulverized.

Example 2: Composition of Food Component According to the Present Invention

One tablespoon (15 g) of the food component as disclosed herein provides:
12 g complete protein
100% daily intake value (DV) of Vitamin B12
15% DV of iron for a female/35% DV for a male
10% DV of Vitamin B2
100% DV of butryate Example 3: Preparation of a Hard Cheese Analogue The food component as disclosed herein is blended with water at ambient temperature and pressure for about 5-10 mins, such as in a Stephan cooker (processed cheese industrial cooker available from Stephan Machinery GmbH. Germany), until no visible clumps are present.

Coconut oil is slowly melted in a beaker in a water bath and then blended with gum (such as lecithin) and colorant. Starches and any additional powder, as desired, is added to the beaker.

The contents of the beaker are added to the Stephan cooker, together with any other desired ingredients except for acid and flavorant and blended for about 2 minutes at ambient temperature and pressure.

A glycol bath is connected to the jacket of the Stephan cooker and the contents of the cooker are heated to about 185° F. The Stephan cooker is set to speed 9 and the sides scraped down. The temperature is monitored at intervals. Once the temperature reaches about 194° F., acid and flavorants are added. Mixing is carried out without further heating for about 1 minute.

The resultant mixture is poured into a suitable container, the surface covered with plastic wrap to prevent drying and the container placed in a refrigerated environment to cool.

Example 4: Preparation of a Soft Cheese Analogue

The food component as disclosed herein is blended with water at ambient temperature and pressure for about 5-10 mins, such as in a Stephan cooker, until no visible clumps are present.

Coconut oil is slowly melted in a beaker in a water bath and then blended with gum and colorant. Starches and any additional powder, as desired, is added to the beaker.

The contents of the beaker are added to the Stephan cooker, together with any other desired ingredients except for acid and flavorant and blended for about 2 minutes at ambient temperature and pressure.

A glycol bath is connected to the jacket of the Stephan cooker and the contents of the cooker are heated to about 185° F., then acid and liquid flavorants as desired are added. The Stephan cooker is set to speed 9 and the sides scraped down. The temperature is monitored at intervals. Once the temperature reaches about 194° F., the mixture is cooled and the cooled mixture is beaten with a paddle mixer to provide a fluffy consistency.

Example 5: Nutritional Values of Exemplary Cheese Analogues According to the Present Invention a. Soft Cheese Analogue
Serving size: 28 g
Amount per serving:

| Calories: 70 | | |
|---|---|---|
| | | % daily value |
| Total fat | 6 g | 8% |
| Saturated fat | 6 g | 30% |
| Trans fat | 0 g | |
| Cholesterol | 0 mg | |
| Sodium | 140 mg | 6% |
| Total carbohydrate | 4 g | 1% |
| Dietary fiber | 0 g | |
| Total sugars | 0 g | |
| Protein | 1 g | |
| Vitamin D | 0 g | |
| Calcium | 144 mg | 10% |
| Iron | 0 g | | b. Hard Cheese (Cheddar Cheese) Analogue
Serving size: 28 g
Amount per serving:

| Calories: 70 | | |
|---|---|---|
| | | % daily value |
| Total fat | 6 g | 8% |
| Saturated fat | 6 g | 30% |
| Trans fat | 0 g | |
| Cholesterol | 0 mg | |
| Sodium | 140 mg | 6% |
| Total carbohydrate | 4 g | 1% |
| Dietary fiber | 0 g | |
| Total sugars | 0 g | |
| Protein | 1 g | |
| Vitamin D | 0 g | |
| Calcium | 144 mg | 10% |

-continued

| Calories: 70 | | |
|---|---|---|
| | | % daily value |
| Iron | 0 g | |
| Potassium | 4 mg | | c. Slumping Cheese Analogue
Serving size: 28 g
Amount per serving:

| Calories: 60 | | |
|---|---|---|
| | | % daily value |
| Total fat | 5 g | 6% |
| Saturated fat | 4.5 g | 23% |
| Trans fat | 0 g | |
| Cholesterol | 0 mg | |
| Sodium | 150 mg | 7% |
| Total carbohydrate | 3 g | 1% |
| Dietary fiber | 0 g | |
| Total sugars | 0 g | |
| Protein | 1 g | |
| Vitamin D | 0 g | |
| Calcium | 147 mg | 10% |
| Iron | 0 g | |
| Potassium | 2 mg | |

Example 6: Exemplary Milk Beverage Analogues According to the Present Invention a. Oat Milk Beverage The food component as disclosed herein, having a protein concentration of 85% and a vitamin B12 concentration of 15 mcg/100 g was provided in powder form. Also provided was oat milk (Oatly® milk alternative, Oatly, Sweden) having 2.4 gr protein and 0.91 mcg vitamin B12 (36% DV) per serving of 240 ml. 10.8 gr of the powder was blended with the oat milk to form an enriched product containing 11.6 gr protein and 2.53 mcg Vitamin B12 (>100 DV) per serving.

The beverage was homogenized to provide a particle size of about 50 microns.

b. Almond Milk Beverage

The food component as disclosed herein, having a protein concentration of 85% and a vitamin B12 concentration of 15 mcg/100 g was provided in powder form. Also provided was Califia® almond milk having 1 gr protein per serving of 240 ml and no vitamin B12. 16 gr of the powder was blended with almond milk to form an enriched product containing 14.7 gr protein and 2.4 mcg Vitamin B12 (100 DV) per serving.

Example 7: Taste Analysis of Exemplary Milk Beverage Analogues According to the Present Invention The oat milk beverage and the almond milk beverage of Example 6 were analyzed by an expert taster and compared to the respective oat milk and almond beverages in the absence of the food component of the present invention.

The reported conclusions are as follows:

a. Oat Milk
i. Oat Milk Alone
Mellow flavor, a hint of dairy note and oat after note. A little thin in the mouth.

ii. Oat Milk with Food Component According to the Present Invention
Stronger aroma that can be interpreted as dairy/cream or hint of cheese (cheddar); flavor is of full fat milk with a stronger dairy note with sweet/cream note and a hint of mocca. Reacher body with a little chalkiness. After shaking hard, really great, creamy coating on the mouth.

b. Almond Milk
i. Almond Milk Alone
Aroma with little almond extract note; flavor is closer to raw hazelnut and some green almonds, mildly sweet with watery mouthfeel.

ii. Almond Milk with Food Component According to the Present Invention
Strong aroma of savory/umami with some coffee; flavor is sweet, mellowing the almond/hazelnut notes and increasing the cream dairy notes, providing a more natural dairy flavor. Mouthfeel is almost like heavy cream—heavier/thicker in the mouth with lingering coating. Some umami lingering after taste.

The invention claimed is:

1. A food component comprising cells of at least one bacterium, said cells comprising a crude protein concentration of at least 60 wt. % of a total dry weight of said cells and a nucleic acid concentration of less than about 5 wt. % of a total dry weight of said cells, wherein at least 50% of a total number of said cells are dead cells and wherein at least 50 wt. % of said cells are intact cells.

2. The food component of claim 1, wherein said at least one bacterium is an anaerobic bacterium.

3. The food component of claim 1, said cells comprising at east one selected from the group consisting of:
   (i) essential amino acids at a concentration of at least 20 wt. % of a total dry weight of said cells;
   (ii) branched-chain amino acids at a concentration of at least 10 wt. % of a total dry weight of said cells;
   (iii) at least one mineral selected from the group consisting of calcium, iron, zinc, copper, manganese, molybdenum, selenium and combinations thereof;
   (iv) Vitamin B12 at a concentration of from about 1 to about 20 microgram per 100 gram dry weight of said cells;
   (v) peptidoglycan at a concentration of from about 0.1 to about 10 wt. % of a total dry weight of said cells; and
   (vi) butyric acid concentration of from about 0.001 wt. % to about 1 wt. % of the total dry weight of the food component.

4. The food component of claim 1, characterized by comprising at least one selected from the group consisting of:
   (i) having protease activity of about 1 milli Anson Unit;
   (ii) being in the form of a powder having particle size of from about 1 to about 150 microns;
   (iii) having a fat concentration of less than about 1 wt. % of the total dry weight of said cells;
   (iv) having a pH of greater than about 6.7;
   (v) comprising less than 0.1 wt. % casein of the total dry weight of the food component; and
   (vi) said bacterium being a naturally occurring bacterium.

5. A food or a beverage comprising the food component of claim 1.

6. The food or beverage of claim 5, further comprising at least one selected from the group consisting of:
   (i) a flavorant;
   (ii) a fruit;
   (iii) a fat at from about 0.5 wt. % to about 30 wt. % of the total weight of the food or beverage;

(iv) a carbohydrate, at from about 5 wt. % to about 20 wt. % of the total weight of the food or beverage;
(v) at least one amino acid;
(vi) at least 0.05 wt. % of butyrate and/or butyrin; and
(vii) a plant protein at a concentration of from about 20 wt. % to about 80 wt. % of the weight of the total protein content.

7. The food or beverage of claim 5, comprising at least one selected from the group consisting of:
(i) comprising an oil-in-water emulsion, wherein said protein stabilizes said emulsion on the interface of oil droplets;
(ii) being a homogenized product;
(iii) comprising an edible oil;
(iv) comprising a foam;
(v) comprising dispersed particles of said bacterium;
(vi) having a pH of greater than about 6.7;
(vii) being a meat or fish analogue;
(viii) being an extruded meat product; and
(ix) having a protein concentration of at least 5 wt. % of the total weight of the food.

8. The food or beverage of claim 5, being a dairy analogue.

9. The food or beverage of claim 8, wherein said dairy analogue is an analogue of a dairy product selected from the group consisting of a cheese, a milk beverage, a yoghurt, a cream, a whipped cream, an ice-cream, dessert, and a butter.

10. The food or beverage of claim 8, wherein said dairy analogue has a protein concentration of at least 2 wt. % of the total weight of the dairy analogue.

11. A beverage comprising the food component of claim 1 and at least one selected from the group consisting of oat milk and almond milk.

12. A method of preparing a beverage, comprising blending the food component of claim 1 with a plant-based milk to form a blend and optionally homogenizing said blend.

13. The method of claim 12, wherein said plant-based milk is selected from the group consisting of oat milk and almond milk.

14. A food binder comprising the food component of claim 1.

15. A meat analogue comprising the food binder of claim 14.

16. The meat analogue of claim 15, having a methyl cellulose content of less than about 1 wt. %.

17. A method for the manufacture of the food component of claim 1, comprising culturing said cells of at least one bacterium in a fermentation medium to obtain a fermentation medium comprising a biomass; separating said biomass from said fermentation medium containing said biomass to obtain separated biomass; and killing at least 50% of cells of said separated biomass.

18. The method of claim 17, wherein said separating comprises microfiltration.

19. The method of claim 17, further comprising heating said separated biomass to a temperature of at least 135° C. for a period of at least 2 seconds.

20. The method of claim 17, further comprising drying said separated biomass to provide a dry biomass having a water content of no greater than 5 wt. %.

* * * * *